(12) United States Patent
Gu et al.

(10) Patent No.: US 11,311,272 B2
(45) Date of Patent: Apr. 26, 2022

(54) ULTRASONIC PROBE

(71) Applicant: SAMSUNG MEDISON CO., LTD., Gangwon-do (KR)

(72) Inventors: Jin Ho Gu, Yongin-si (KR); Gil-Ju Jin, Seoul (KR)

(73) Assignee: SAMSUNG MEDISON CO., LTD., Gangwon-Do (KR)

( * ) Notice: Subject to any disclaimer, the term of this patent is extended or adjusted under 35 U.S.C. 154(b) by 440 days.

(21) Appl. No.: 16/263,617

(22) Filed: Jan. 31, 2019

(65) Prior Publication Data

US 2019/0231309 A1 Aug. 1, 2019

(30) Foreign Application Priority Data

Jan. 31, 2018 (KR) .................. 10-2018-0011762

(51) Int. Cl.
*A61B 8/00* (2006.01)
*G01S 7/52* (2006.01)
*F28D 21/00* (2006.01)

(52) U.S. Cl.
CPC .......... *A61B 8/4444* (2013.01); *A61B 8/4455* (2013.01); *A61B 8/4472* (2013.01); *A61B 8/546* (2013.01); *F28D 21/00* (2013.01); *G01S 7/5208* (2013.01); *F28D 2021/0029* (2013.01)

(58) Field of Classification Search
None
See application file for complete search history.

(56) References Cited

U.S. PATENT DOCUMENTS

| | | | |
|---|---|---|---|
| 5,560,362 A * | 10/1996 | Sliwa, Jr. | A61B 8/546 600/439 |
| 5,961,465 A | 10/1999 | Kelly, Jr. et al. | |
| 2014/0058270 A1 | 2/2014 | Davidsen et al. | |
| 2015/0351727 A1 | 12/2015 | Nieminen et al. | |
| 2016/0242747 A1 | 8/2016 | Siedemburg et al. | |
| 2018/0125461 A1* | 5/2018 | Clark | G10K 11/004 |

FOREIGN PATENT DOCUMENTS

| | | |
|---|---|---|
| KR | 10-2010-0047395 A | 5/2010 |
| KR | 10-2010-0047437 A | 5/2010 |
| KR | 10-2013-0122202 A | 11/2013 |
| WO | 2015/129938 A1 | 9/2015 |
| WO | 2015/147355 A1 | 10/2015 |

OTHER PUBLICATIONS

Extended European Search Report dated Feb. 5, 2019 issued in European Patent Application No. 18189376.9.
European Search Report dated Apr. 14, 2020 issued in European Patent Application No. 18189376.9.

\* cited by examiner

*Primary Examiner* — Colin T. Sakamoto
(74) *Attorney, Agent, or Firm* — Morgan, Lewis & Bockius LLP

(57) ABSTRACT

Disclosed herein is an ultrasonic probe having improved heat dissipation capability. The ultrasonic probe includes a housing, an acoustic module disposed in the housing, and configured to transmit an ultrasonic signal to an object and receive an signal reflected from the object, an electronic circuit disposed in the housing and electrically connected to the acoustic module to drive the acoustic module, and a hole communicating an outside of the housing with the electronic circuit so that the electronic circuit is cooled by air outside the housing.

10 Claims, 10 Drawing Sheets

ULTRASONIC PROBE

CROSS-REFERENCE TO RELATED APPLICATION

This application is based on and claims priority under 35 U.S.C. § 119 to Korean Patent Application No. 10-2018-0011762, filed on Jan. 31, 2018 in the Korean Intellectual Property Office, the disclosure of which is incorporated by reference herein in its entirety.

BACKGROUND

1. Field

The disclosure relates to an ultrasonic probe to generate an image of the inside of an object by using ultrasonic, and more particularly, to an ultrasonic probe having improved heat dissipation capability.

2. Description of Related Art

An ultrasonic imaging apparatus radiates ultrasonic signals toward a target region inside an object from a surface of the object and then collects reflected ultrasonic signals (ultrasonic echo signals) to non-invasively acquire tomograms of soft tissues or images of blood streams using information thereon.

Ultrasonic imaging apparatuses are relatively small in size and inexpensive, display an image in real time, and have high safety due to no radiation exposure as compared with other diagnostic imaging apparatuses such as X-ray diagnosis apparatuses, X-ray computerized tomography (CT) scanners, magnetic resonance imaging (MRI) apparatuses, and nuclear medicine diagnosis apparatuses. Thus, ultrasonic imaging apparatuses have been widely used for heart diagnosis, celiac diagnosis, urinary diagnosis, and obstetric diagnosis.

An ultrasonic imaging apparatus includes an ultrasonic probe that transmits ultrasonic signals to an object and receives ultrasonic echo signals reflected by the object to acquire an ultrasonic image of the object and a main body that generates an image of the inside of the object by using the ultrasonic echo signals received by the ultrasonic probe. In general, a wire is provided between the ultrasonic probe and the main body for connecting them. This is called a wired ultrasonic imaging apparatus. In the case of the wired ultrasonic imaging apparatus, an image processing unit is generally disposed inside the main body.

Recently, a wireless ultrasonic imaging apparatus has been developed. In the case of the wireless ultrasonic imaging apparatus, since the ultrasonic probe and the main body are connected through wireless communication, no wire is provided between the ultrasonic probe and the main body. Thus, the portability of the ultrasonic probe is improved.

In the wireless ultrasonic imaging apparatus, the image processing unit may be disposed inside the ultrasonic probe. Such an image processing unit may generate heat during operation. The heat generated by the image processing unit is higher than the heat generated by the transducer, and a more direct and effective heat dissipating structure is required.

SUMMARY

Therefore, it is an aspect of the present disclosure to provide an ultrasonic probe having improved heat dissipation capability.

It is another aspect of the present disclosure to provide an ultrasonic probe having a direct heat dissipation structure through convection.

It is another aspect of the present disclosure to provide an ultrasonic probe for discharging heat inside a housing through a hole formed in a surface of the housing.

Additional aspects of the present disclosure will be set forth in part in the description which follows and, in part, will be obvious from the description, or may be learned by practice of the present disclosure.

In accordance with an aspect of the present disclosure an ultrasonic probe includes a housing, an acoustic module disposed in the housing, and configured to transmit an ultrasonic signal to an object and receive an signal reflected from the object, an electronic circuit disposed in the housing and electrically connected to the acoustic module to drive the acoustic module, and a hole communicating an outside of the housing with the electronic circuit so that the electronic circuit is cooled by air outside the housing.

The electronic circuit may include a heating element, and the hole and the heating element may be arranged to face each other.

The heating element may include at least one of a beam former and a central processing unit (CPU).

The hole may include a plurality of holes.

The housing may further include a protective net configured to cover the hole.

The ultrasonic probe may further include a heat dissipating member disposed on one surface of the heat element to extend a heat dissipating area of the heating element.

The heat dissipating member may include a radiation fin which is in contact with the heating element to exchange heat with the heating element.

The ultrasonic probe may further include a sealing member sealing the space between the housing and the heating element to prevent moisture from outside the housing from penetrating into the inside of the housing through the hole.

The sealing member may include an O-ring.

When a traveling direction of the echo signal transmitted from and received by the acoustic module is a first direction, the hole and the heating element may be disposed along a second direction intersecting the first direction.

The housing may include at least one hollow portion, and the hole may be formed on one surface of the hollow portion.

The housing may include a recessed portion recessed toward the inside of the housing, and the hole may be formed on one surface of the recessed portion.

BRIEF DESCRIPTION OF THE DRAWINGS

These and/or other aspects of the disclosure will become apparent and more readily appreciated from the following description of embodiments, taken in conjunction with the accompanying drawings of which.

DETAILED DESCRIPTION

Figure 1:
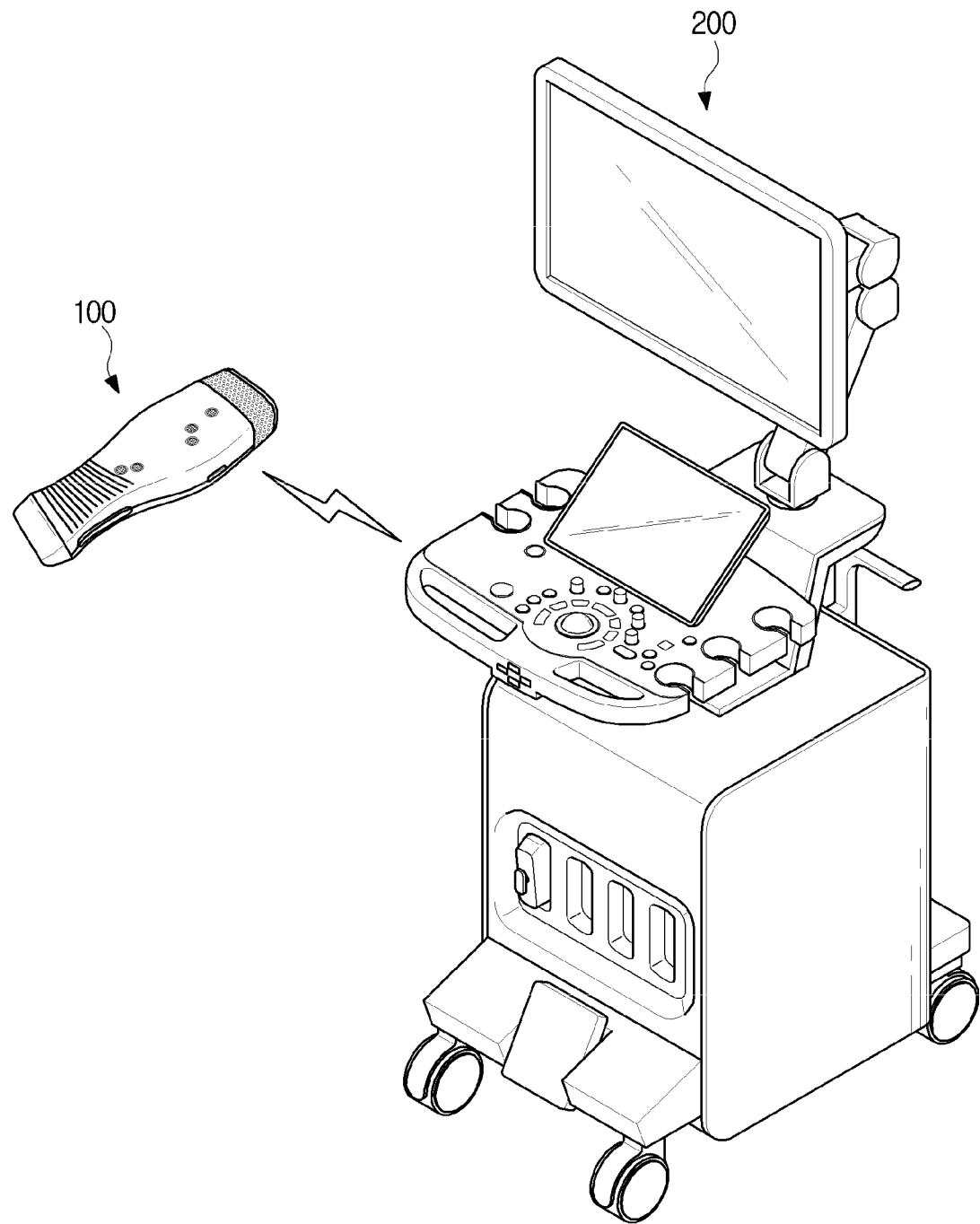
FIG. 1 is a view illustrating an ultrasonic imaging apparatus according to an embodiment.

Embodiments described in the present disclosure and configurations shown in the drawings are merely examples of the embodiments of the present disclosure, and may be modified in various different ways at the time of filing of the present application to replace the embodiments and drawings of the present disclosure.

In addition, the same reference numerals or signs shown in the drawings of the present disclosure indicate elements or components performing substantially the same function.

Also, the terms used herein are used to describe the embodiments and are not intended to limit and/or restrict the present disclosure. The singular forms "a," "an" and "the" are intended to include the plural forms as well, unless the context clearly indicates otherwise. In this present disclosure, the terms "including", "having", and the like are used to specify features, numbers, steps, operations, elements, components, or combinations thereof, but do not preclude the presence or addition of one or more of the features, elements, steps, operations, elements, components, or combinations thereof.

It will be understood that, although the terms first, second, third, etc., may be used herein to describe various elements, but elements are not limited by these terms. These terms are only used to distinguish one element from another element. For example, without departing from the scope of the present disclosure, a first element may be termed as a second element, and a second element may be termed as a first element. The term of "and/or" includes a plurality of combinations of relevant items or any one item among a plurality of relevant items.

Hereinafter, embodiments according to the present disclosure will be described in detail with reference to the accompanying drawings.

FIG. 1 is a view illustrating an ultrasonic imaging apparatus according to an embodiment.

An ultrasonic probe 100 may transmit an ultrasonic signal to an object, receive an echo signal reflected from the object, and form a received signal. The ultrasonic probe 100 may process the received signal to generate ultrasonic image data. The ultrasonic probe 100 may transmit the generated ultrasonic image data to an ultrasonic diagnostic apparatus 200. The ultrasonic probe 100 may be wirelessly connected to the ultrasonic diagnostic apparatus 200 by using a wireless communication method. Hereinafter, an ultrasonic probe 100 connected wirelessly to the ultrasonic diagnostic apparatus 200 will be described as an example.

The ultrasonic diagnostic apparatus 200 may be connected to the ultrasonic probe 100 wirelessly and may display an ultrasonic image by using the ultrasonic image data received from the ultrasonic probe 100. For example, the ultrasonic diagnostic apparatus 200 may represent not only an ultrasonic image of a gray scale obtained by scanning the object according to an A mode (amplitude mode), a B mode (brightness mode), and an M mode (motion mode), but also a movement of the object, as a Doppler image. In an embodiment, the ultrasonic diagnosis apparatus 200 may be embodied not only as a cart type but also as a portable type.

A portable ultrasonic diagnosis apparatus may include a picture archiving and communication system (PACS) viewer, hand-carried cardiac ultrasonic (HCU) equipment, smart phones, laptop computers, personal digital assistants (PDAs), tablet personal computers (PCs), etc., but is not limited thereto.

In an embodiment, the ultrasonic diagnosis apparatus 200 may be an apparatus for generating an ultrasonic image by processing the ultrasonic image data received from the ultrasonic probe 100 and displaying a generated image, or an apparatus that simply embodies only an image display function without a separate image processing function. In other words, the ultrasonic diagnosis apparatus 200 may include a display apparatus that receives an image from the ultrasonic probe 100 and displays the received image on a screen without additional processing.

The ultrasonic probe 100 may be wirelessly connected to the ultrasonic diagnosis apparatus 200 by a data communication method. In an embodiment, the ultrasonic probe 100 may be wirelessly connected to the ultrasonic diagnosis apparatus 200 by a 60 GHz millimeter wave (mm Wave) short-distance wireless communication method. However, the present disclosure is not limited thereto, and the ultrasonic probe 100 may be connected to the ultrasonic diagnosis apparatus 200 by using at least one of data communication methods, for example, wireless local area network (LAN), Wi-Fi, Bluetooth, Zigbee, Wi-Fi direct (WFD), ultra wideband (UWB), infrared data association (IrDA), Bluetooth low energy (BLE), near field communication (NFC), wireless broadband Internet (Wibro), world interoperability for microwave access (WiMAX), shared wireless access protocol (SWAP), wireless gigabit alliance (WiGig), and radio frequency (RF) communications.

Figure 2:
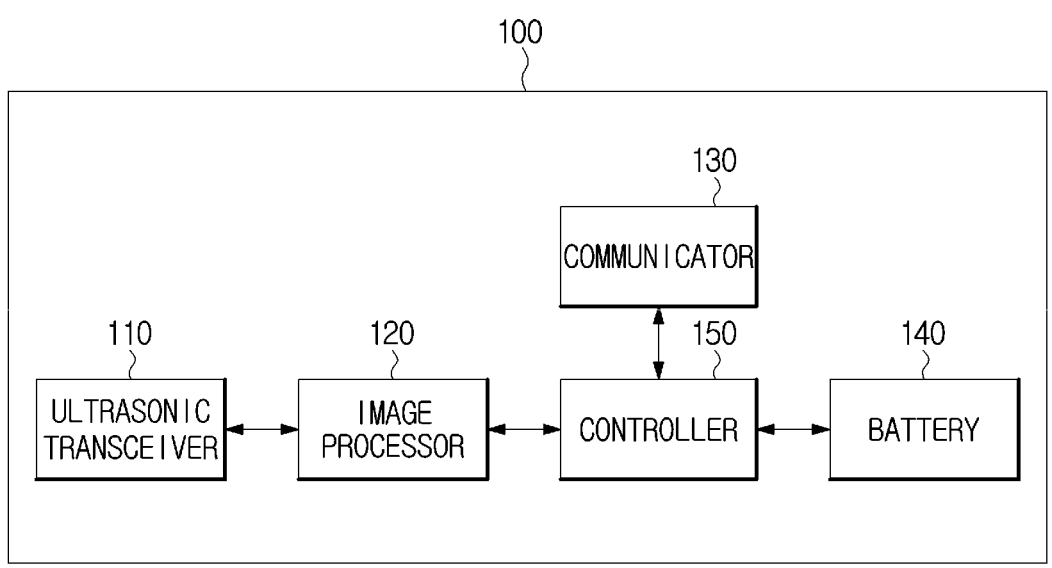
FIG. 2 is a block diagram illustrating a structure of an ultrasonic probe according to an embodiment.

FIG. 2 is a block diagram illustrating a structure of an ultrasonic probe 100 according to an embodiment.

Referring to FIG. 2, the ultrasonic probe 100 may include an ultrasonic transceiver 110, an image processor 120, a communicator 130, a battery 140, and a controller 150.

The ultrasonic transceiver 110 transmits an ultrasonic signal to the object and receives an echo signal reflected from the object. The ultrasonic transceiver 110 may generate a pulse for forming a transmissive ultrasonic wave according to a certain pulse repetition frequency (PRF). The ultrasonic transceiver 110 may apply a delay time to determine transmission directionality to the pulse. Each pulse to which the delay time is applied may correspond to each of a plurality of piezoelectric vibrators included in a transducer. The ultrasonic transceiver 110 may transmit an ultrasonic signal to the object by applying the pulse corresponding to each of the piezoelectric vibrators at a timing corresponding to each pulse to which the delay time is applied.

The transducer is not limited to piezoelectric vibrators. An embodiment of the transducer may include a magnetostrictive ultrasonic transducer that utilizes the magnetostrictive effect of a magnetic substance or a capacitive micromachined ultrasonic tranceducer that transmits and receives ultrasonic waves using vibration of hundreds or thousands of micro-machined thin films.

The image processor 120 may generate ultrasonic image data corresponding to a data type wherein the data type is determined by the controller 150 based on the echo signal received from the ultrasonic transceiver 110. The image processor 120 may generate ultrasonic image data by processing the echo signal reflected from the object. The image processor 120 may amplify the echo signal for each channel and perform analog-digital (AD) conversion on an amplified echo signal. The image processor 120 may apply the delay time to determine reception directionality to a digitally converted echo signal. By including the image processor 120 in the ultrasonic probe 100, a capacity of data transmitted by the communicator 130 may be reduced. However, as described later, since the image processor 120 is included in the ultrasonic probe 100, a temperature inside the ultrasonic probe 100 may be increased. This is because a large amount of heat is generated during an operation of the image processor 120.

The communicator 130 may transmit the ultrasonic image data generated by the image processor 120 to the ultrasonic diagnosis apparatus 200. In an embodiment, the communicator 130 may transmit raw data, which is generated by performing analog-digital conversion on the echo signal amplified by the image processor 120, to the ultrasonic diagnosis apparatus 200. In an embodiment, the communicator 130 may transmit at least one piece of information about setting of the ultrasonic probe 100 including information about identification of the ultrasonic probe 100, ultrasonic preset setting information, information about a user of the ultrasonic probe 100, and information about an object, to the ultrasonic diagnosis apparatus 200.

The communicator 130 may perform wireless communication with the ultrasonic diagnosis apparatus 200. The communicator 130 may perform data communication with the ultrasonic diagnosis apparatus 200 by at least one of short-distance communication methods including, for example, LAN, Wi-Fi, Bluetooth, Zigbee, WFD, UWB, IrDA, BLE, NFC, Wibro, WiMAX, SWAP, WiGig, and RF communications.

In an embodiment, the communicator 130 may communicate with an external device or server by being connected to a network in a wired or wireless manner. The communicator 130 may exchange data with a hospital server or another medical apparatus in a hospital, which is connected thereto via a PACS. Furthermore, the communicator 130 may perform data communication according to the digital imaging and communications in medicine (DICOM) standard.

The communicator 130 may transmit or receive data related to diagnosis of the object, e.g., an ultrasonic image, ultrasonic data, and Doppler data of the object, via the network and may also transmit or receive medical images captured by another medical apparatus, e.g., a computed tomography (CT) apparatus, a magnetic resonance imaging (MRI) apparatus, or an X-ray apparatus. Furthermore, the communicator 130 may receive information about a diagnosis history or medical treatment schedule of a patient from a server and utilizes the received information to diagnose the patient. Furthermore, the communicator 130 may perform data communication not only with a server or a medical apparatus in a hospital, but also with a portable terminal of a medical doctor or patient.

The battery 140 may supply power needed to operate the ultrasonic probe 100. The battery 140 may include, for example, at least one of lithium-ion (Li-ion), nickelmetal hydride (Ni-MH), lead oxide (PbOx), and sodium-sulfur (Na—S). However, the present disclosure is not limited thereto and the battery 140 may include a material capable of charging, such as, lithium metal oxide, an organic electrode material, and transition metal.

The controller 150 may control the communicator 130 to determine a data communication method used for transmitting the ultrasonic image data generated by the image processor 120 to the ultrasonic diagnosis apparatus 200.

The controller 150 may determine at least one of a wireless communication method, a usable bandwidth, a transmission speed for a communication channel, a communication channel type, and an identifier, which are used by the ultrasonic diagnosis apparatus 200, based on information about the ultrasonic diagnosis apparatus 200.

In an embodiment, the controller 150 may select at least one image processing operation from a plurality of sequential image processing operations, which is to be performed to generate a displayable ultrasonic image from the echo signal, based on the type of determined data. In an embodiment, the controller 150 may obtain the information about the ultrasonic diagnosis apparatus 200 through the communicator 130. The controller 150 may determine the type of data configured to be processed by the ultrasonic diagnosis apparatus 200, based on the information about the ultrasonic diagnosis apparatus 200, and may determine a method of performing data communication with the ultrasonic diagnosis apparatus 200. For example, when raw data, which is generated as the image processor 120 performs AD conversion on the echo signal reflected from the object, is transmitted to the ultrasonic diagnosis apparatus 200, the controller 150 may control the communicator 130 to use a 60 GHz millimeter wave short-distance wireless communication method.

The controller 150 may be a module including at least one of a central processing unit, a microprocessor, a graphic processing unit, random-access memory (RAM), and read-only memory (ROM). In an embodiment, the controller 150 may be embodied by an application processor (AP). In an embodiment, the controller 150 may be embodied by a hardware element such as an FPGA or ASIC. However, the present disclosure is not limited thereto and the controller 150 may include constituent elements such as software constituent elements, object-oriented software constituent elements, class constituent elements, and task constituent elements, processes, functions, attributes, procedures, subroutines, segments of program codes, drivers, firmware, microcodes, circuits, data, databases, data structures, tables, arrays, and variables.

Figure 3:
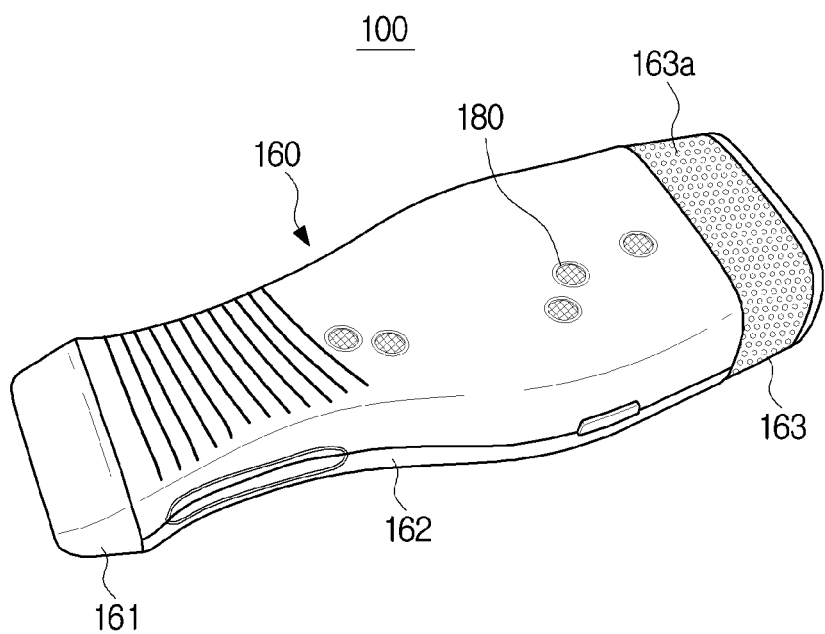
FIG. 3 is a perspective view of an ultrasonic probe according to an embodiment.
Figure 4:
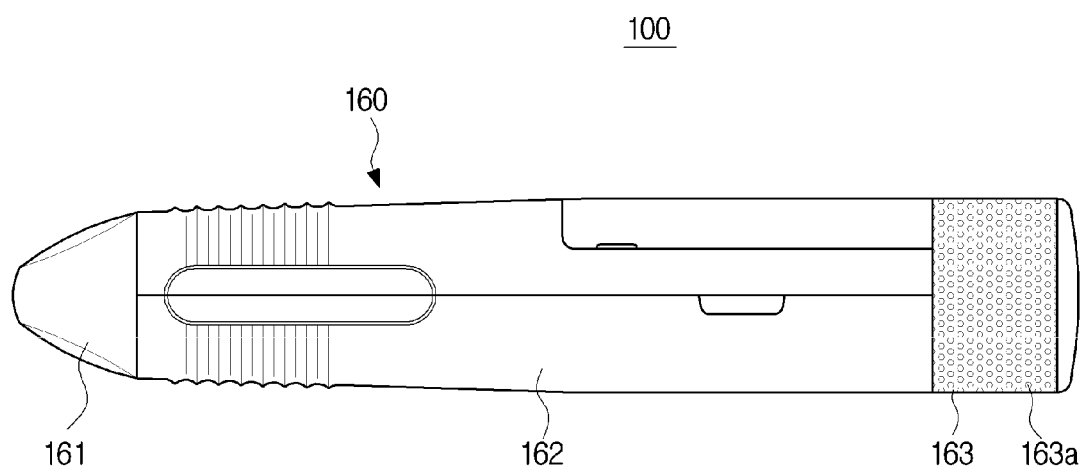
FIG. 4 is a side view of an ultrasonic probe according to an embodiment.
Figure 5:
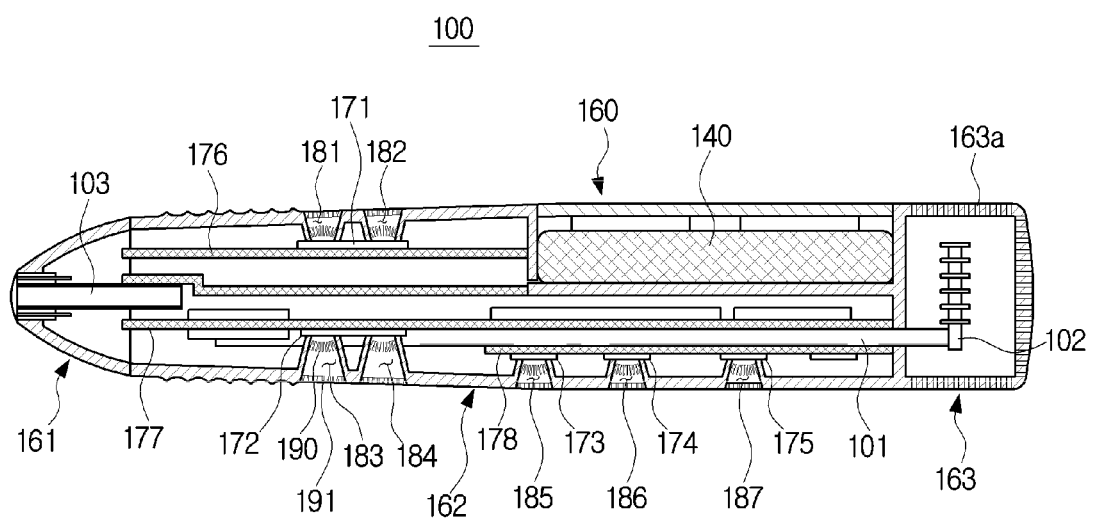
FIG. 5 is a view illustrating an internal structure of an ultrasonic probe according to an embodiment.

FIG. 3 is a perspective view of an ultrasonic probe according to an embodiment. FIG. 4 is a side view of an ultrasonic probe according to an embodiment. FIG. 5 is a view illustrating an internal structure of an ultrasonic probe according to an embodiment.

Referring to FIG. 3 to FIG. 5, the ultrasonic probe 100 may include a housing 160.

The housing 160 may form an external appearance of the ultrasonic probe 100 and may include a head portion 161, a handle portion 162, and a heat dissipating portion 163.

The head portion 161 may be disposed in front of the handle portion 162.

The heat dissipating portion 163 may be disposed behind the handle portion 162. A forward direction may be a direction toward an object, and a rear direction may be the opposite direction of the forward direction.

Inside the housing 160, an ultrasonic transceiver 110 and an electronic circuit may be disposed. The electronic circuit may include the image processor 120, the communicator 130, the battery 140, and the controller 150 described above. For example, an acoustic module 103 (see FIG. 5) of the ultrasonic transceiver 110 may be disposed inside the head portion 161. The electronic circuit may be disposed inside the handle portion 162. That is, the image processor 120, the communicator 130, the battery 140, and the controller 150 may be disposed inside the handle portion 162. However, this is an example, and the arrangement of the components inside the housing 160 may be changed according to design specifications.

During an operation of the ultrasonic probe 100, heat may be generated in a component disposed within the housing 160. For example, during an ultrasonic diagnosis by using the ultrasonic probe 100, heat may be generated in the acoustic module 103 and the image processor 120 disposed inside the housing 160. The temperature of the acoustic module 103 may increase during a process of transmitting the ultrasonic signal or receiving the echo signal, and the temperature of the image processor 120 may increase during an image processing. At this time, the temperature of the image processor 120 may be higher than the temperature of the acoustic module 103. For example, when heat is generated in the acoustic module 103, the temperature of the acoustic module 103 may rise to 40° C. to 50° C. When heat is generated in the image processor 120, the temperature of the image processor 120 may rise to 80° C. to 100° C.

The use of the ultrasonic probe 100 may be restricted if the temperature inside the housing 160 rises to a predetermined temperature or higher due to the acoustic module 103 and the image processor 120. It is necessary to reduce the temperature inside the housing 160 in order to ensure a stable operation of the ultrasonic probe 100 and secure the use time of the ultrasonic probe 100. As described above, since the temperature of the image processor 120 is higher than the temperature of the acoustic module 103, it is more important to lower the temperature of the image processor 120.

According to an aspect of the present disclosure, the housing 160 may include a hole 180 communicating the outside of the housing 160 and the image processor 120. The hole 180 may be formed on one surface of the handle portion 162, and at least one or more holes may be provided. The image processor 120 may perform heat exchange by direct convection with the outside air through the hole 180. It is possible to maximize the heat dissipation effect by adding a heat dissipation structure by convection while using a heat dissipation method using a conductive material such as a conventional heat conduction member. According to an aspect of the present disclosure, it is possible to cool the electronic circuit including an image processor through heat exchange by convection. Thus, the cooling efficiency of the electronic circuit may be improved, and the temperature inside the housing may be lowered to a predetermined temperature or lower. A detailed description thereof will be described later.

The heat dissipating portion 163 may be provided in a mesh structure including a plurality of holes 163a through which air flows in and out. At least a portion of a heat conduction member 101 and a heat dissipating member 102 may be disposed inside the heat dissipating portion 163. The heat dissipating portion 163 provided in a mesh structure may prevent the heat dissipating member 102 from being in contact with a user while being exposed to the air. The heat dissipating member 102 may include a plurality of heat radiation fins that maximize the heat dissipation effect by convection by increasing the heat dissipation area.

The heat conduction member 101 may transfer heat from the electronic circuit to the heat dissipating member 102. The heat conduction member 101 may transfer heat from the front to the rear, thereby lowering the temperature inside the housing 160. However, it is difficult to sufficiently lower the temperature inside the housing 160 by only the heat conduction member 101 and the heat dissipating member 102, and an additional heat dissipating structure is required.

Referring to FIG. 5, the ultrasonic probe 100 may include the housing 160, the acoustic module 103 disposed inside the housing 160, and the electronic circuit disposed inside the housing 160.

The acoustic module 103 may be configured to transmit an ultrasonic signal to an object and receive an echo signal reflected from the object. The electronic circuit may be electrically connected to the acoustic module 103 to drive the acoustic module 103. The electronic circuit may include a plurality of heating elements. For example, the heating element may include a plurality of elements 171 to 175 mounted on the printed circuit boards 176, 177, and 178. The plurality of elements 171 to 175 may include a beam former and/or a central processing unit (CPU).

According to an aspect of the present disclosure, the housing 160 may include a hole 180. The hole 180 may include a plurality of holes 181 to 187.

The plurality of holes 181 to 187 may be formed on one surface of the housing 160. More particularly, the plurality of holes 181 to 187 may be formed on one surface of the handle portion 162.

The plurality of holes 181 to 187 may be arranged to face the plurality of elements 171 to 175, respectively. The plurality of holes 181 to 187 and the plurality of elements 171 to 175 may be arranged in a vertical direction when the head portion 161 and the handle portion 162 are arranged in forward and backward directions. Alternatively, the plurality of holes and the plurality of elements may be arranged in the lateral direction. In other words, when a traveling direction of the echo signal transmitted from and received by the acoustic module 103 is a first direction, each of the plurality of holes 181 to 187 and each of the plurality of elements 171 to 175 may be disposed along a second direction that intersects the first direction.

As shown in FIG. 5, a plurality of holes 181 and 182 may correspond to one heating element (for example, 171). This is to cool the heating element more effectively when a volume of the heating element is large, and the number and size of the holes corresponding to the heating element may be changed according to design specifications.

Figure 6:
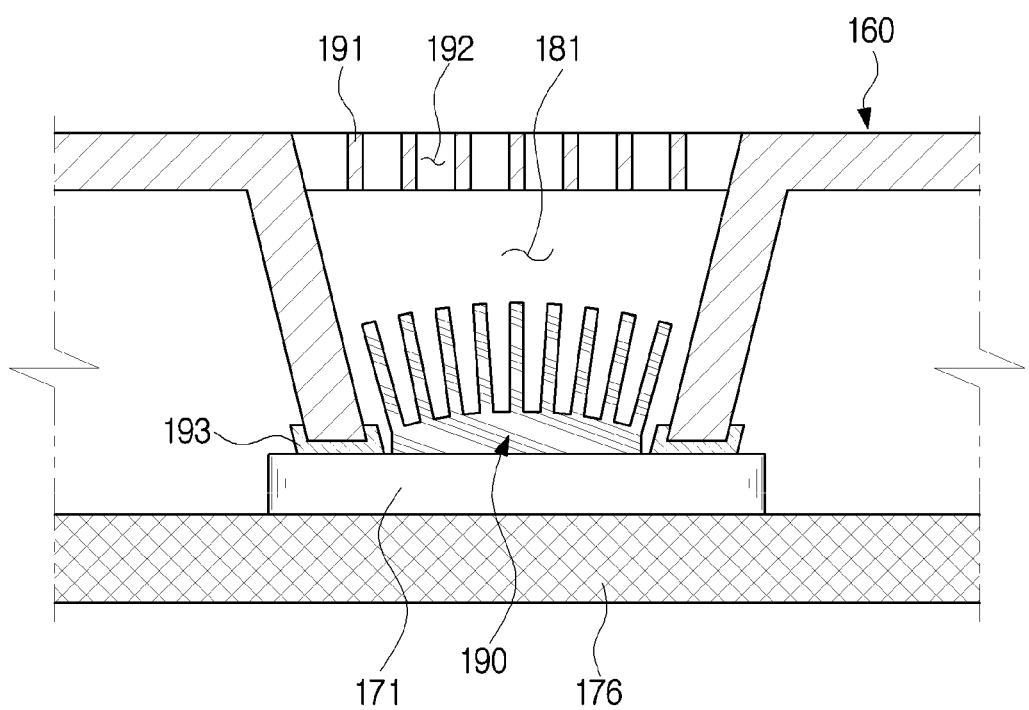
FIG. 6 is an enlarged view of a part of the internal structure of the ultrasonic probe shown in FIG. 5.
Figure 7:
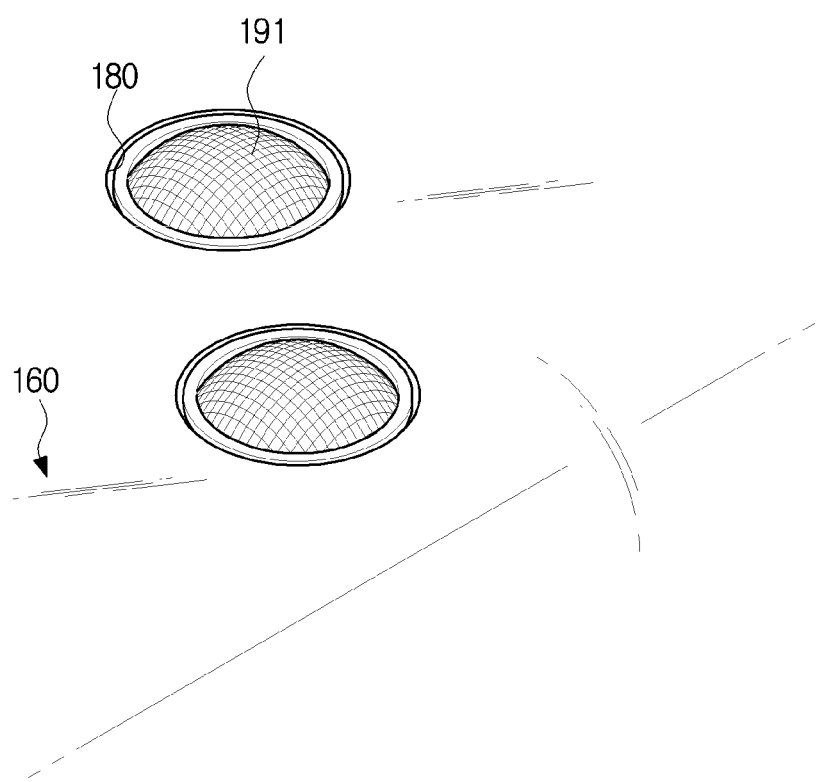
FIG. 7 is an enlarged view of a portion of a housing of an ultrasonic probe according to an embodiment.

FIG. 6 is an enlarged view of a part of the internal structure of the ultrasonic probe shown in FIG. 5. FIG. 7 is an enlarged view of a portion of a housing of an ultrasonic probe according to an embodiment.

Hereinafter, the heat dissipation structure of the present disclosure will be described in detail by taking one hole 181 of the plurality of holes 181 to 187 as an example.

The hole 181 may be formed by bending a portion of the housing 160 toward the inside of the housing 160. An end of the bent portion of the housing 160 may be disposed adjacent to the heating element 171. The bent portion of the housing 160 may cover the periphery of the hole 181. The bent portion of the housing 160 may reduce the size of the gap through which foreign matter such as moisture from the outside of the housing 160 penetrates into the housing 160.

A predetermined gap may be formed between the end of the bent portion of the housing 160 and the heating element 171. Accordingly, moisture and foreign matter from the outside of the housing 160 may penetrate into the inside of the housing 160. A sealing member 193 may be provided between the heating element 171 and the housing 160 to seal the gap. By providing the sealing member 193, the outside of the housing 160 and the inside of the housing 160 may be sealed. The sealing member 193 may be provided in various ways. For example, the sealing member 193 may include an O-ring. Further, the sealing member 193 may be made of a material resistant to heat and having elasticity. An additional sealing grease such as silicone or gel may be applied between the sealing member 193 and the heating element 171.

The heating element 171 may perform heat exchange by direct convection with the outside air introduced through the hole 181. Thus, the heating element 171 may be cooled. The heat dissipating member 190 may be provided to improve the cooling efficiency or heat dissipation efficiency of the heating element 171. The heat dissipating member 190 may be disposed on one surface of the heating element 171 and may be in contact with the heating element 171. Thermal grease may be added to a portion that comes in contact with the heating element for effective thermal conduction. The heat dissipating member 190 may expand the heat dissipating area of the heating element 171. For example, the heat dissipating member 190 may include a radiation fin.

Referring to FIG. 6 and FIG. 7, the housing 160 may further include a protective net 191 configured to cover the hole 181. The protective net 191 may include a plurality of holes 192. The protective net 191 may prevent a portion of the user's body such as a finger of the user from being in contact with the heating element 171 through the hole 181 and also may prevent the foreign matter from flowing from the outside. As described above, the temperature of the heating element 171 including the image processor may rise to 80° C. to 100° C. When a portion of the user's body directly contacts the high-temperature of the heating element 171, the user may suffer burns. In order to prevent this, the protective net 191 covers the hole 181.

In addition, the hole 181 may be provided in a predetermined size or less to prevent a body part such as a user's finger from passing through. For example, a diameter of the hole 181 may be set to 1 cm or less. As described above, since the protective net 191 may cover the hole 181, the size of the hole 181 may be changed according to the design specification.

Figure 8:
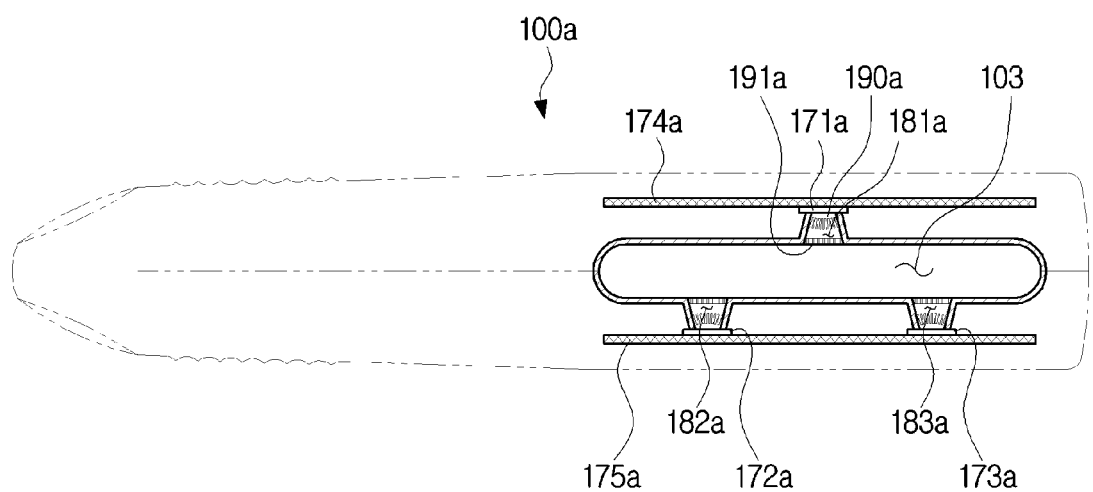
FIG. 8 is a view illustrating an ultrasonic probe according to another embodiment.

FIG. 8 is a view illustrating an ultrasonic probe according to another embodiment.

Referring to FIG. 8, an ultrasonic probe 100*a* according to another embodiment of the present disclosure may include a hollow portion 103. The hollow portion 103 may be configured to penetrate the ultrasonic probe 100*a*. As shown in the FIG. 8, the hollow portion 103 may penetrate the side surface of the ultrasonic probe 100*a*. Alternatively, the hollow portion may penetrate an upper surface or a lower surface of the ultrasonic probe.

The ultrasonic probe 100*a* may include holes 181*a* to 183*a* arranged to face the heating elements 171*a* to 173*a* inside the housing. The number of holes may be changed according to the design specification.

Each of the plurality of holes 181*a* to 183*a* may be provided on either side of the hollow portion. The height of the hollow portion 103 (the length in the vertical direction in FIG. 8) may be set to such a size that the user's finger cannot penetrate. For example, the height of the hollow portion 103 may be 1 cm or less. Since the protective net 191*a* covering each of the plurality of holes 181*a* to 183*a* may be provided, the height of the hollow portion 103 may vary according to design specifications.

When one surface of the hollow portion 103 provided with a first hole 181*a* is an upper surface of the hollow portion 103, one surface of the hollow portion 103 provided with a second hole 182*a* and a third hole 183*a* may be referred to as a lower surface of the hollow portion 103. The holes provided on the upper surface of the hollow portion 103 and the holes provided on the lower surface of the hollow portion 103 may be arranged so as not to face each other.

Figure 9:
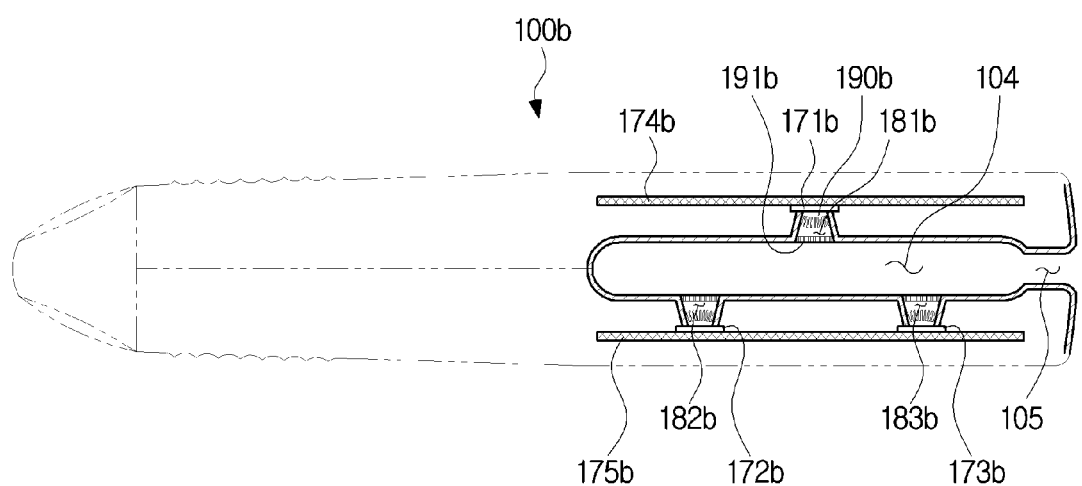
FIG. 9 is a view illustrating an ultrasonic probe according to another embodiment.

FIG. 9 is a view illustrating an ultrasonic probe according to another embodiment.

Referring to FIG. 9, an ultrasonic probe 100*b* according to another embodiment may include a hollow portion 104 having one side opened. In the ultrasonic probe 100*b* according to another embodiment, one side of the hollow portion 104 may be opened. When one side of the opened hollow portion 104 is referred to as a cutout portion 105, the hollow portion 104 and the cutout portion 105 may collectively be referred to as a depressed portion.

The ultrasonic probe 100*b* according to another embodiment may allow outside air to flow in or out through not only the hollow portion 104 but also the cutout portion 105. As a result, the circulation of air may be more effectively performed, and the cooling efficiency or heat dissipation efficiency of the heating elements 171*a* to 173*b* may be increased.

Figure 10:
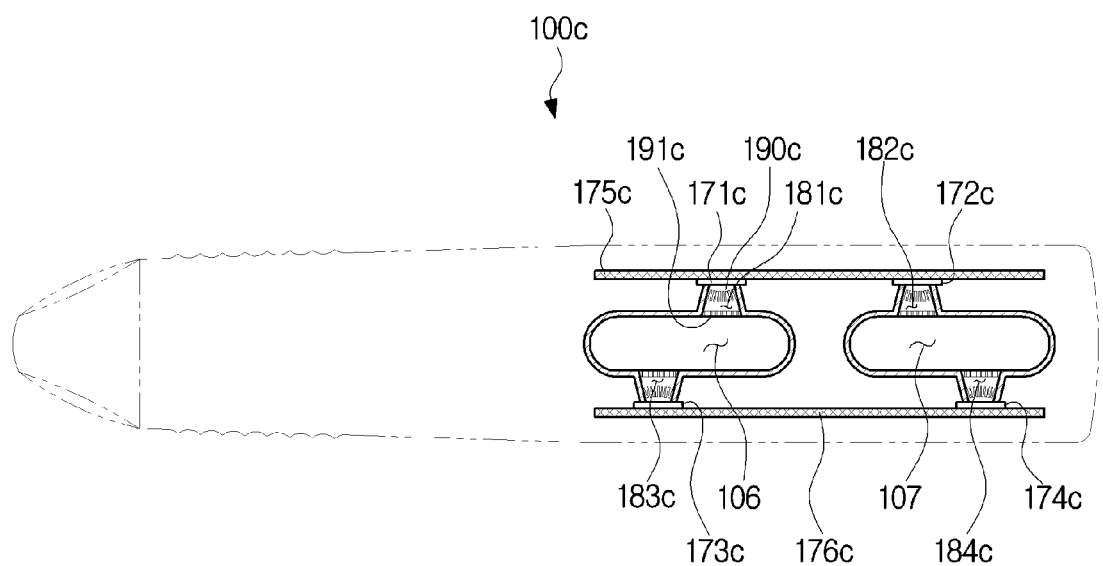
FIG. 10 is a view illustrating an ultrasonic probe according to another embodiment.

FIG. 10 is a view illustrating an ultrasonic probe according to another embodiment.

Referring to FIG. 10, the ultrasonic probe 100*c* according to another embodiment of the present disclosure may include a plurality of hollow portions 106 and 107.

Although FIG. 10 shows that two hollow portions are provided, this is an example and three or more hollow portions may be provided.

As shown in FIG. 10, a first hole 181*c* and a second hole 182*c* may be provided in a first hollow portion 106 and a third hole 183*c* and a fourth hole 184*c* may be provided in a second hollow portion 107. Alternatively, the number and distribution of the holes may be varied in various manners, depending on the embodiment, such that three or more holes may be provided in the first hollow portion 106 and one hole may be provided in the second hollow portion 107.

As is apparent from the above description, an ultrasonic probe with improved heat dissipation capability may be provided.

As is apparent from the above description, an ultrasonic probe with direct heat dissipation structure through convection may be provided.

As is apparent from the above description, an ultrasonic probe for discharging heat inside the housing through holes formed in a surface of the housing may be provided.

Although a few embodiments of the present disclosure have been shown and described, it would be appreciated by those skilled in the art that changes may be made in these embodiments without departing from the principles and spirit of the disclosure, the scope of which is defined in the claims and their equivalents.

What is claimed is:

1. An ultrasonic probe comprising:
   a housing;
   an acoustic module disposed in the housing, and configured to transmit an ultrasonic signal to an object and receive an echo signal reflected from the object;
   an electronic circuit, comprising a heating element, disposed in the housing and electrically connected to the acoustic module to drive the acoustic module;
   a hole fluidly communicating an outside of the housing with the electronic circuit so that the electronic circuit is cooled by air outside the housing;
   a sealing member configured to seal a space between the housing and the heating element to prevent the moisture from the outside the housing from penetrating into an inside of the housing through the hole; and a heat dissipating member disposed on one surface of the heating element to extend a heat dissipating area of the electronic circuit
wherein a portion of the housing is bent toward the inside of the housing to define the hole, and the heat dissipating member is accommodated inside the hole.

2. The ultrasonic probe of claim 1, wherein the hole and the heating element are arranged to face each other.

3. The ultrasonic probe of claim 2, wherein the heating element comprises at least one of a beam former and a central processing unit (CPU).

4. The ultrasonic probe of claim 1, wherein the hole comprises a plurality of holes and each of the plurality of holes communicates the electronic circuit with the outside of the housing.

5. The ultrasonic probe of claim 1, wherein the housing further comprises a protective net configured to cover the hole.

6. The ultrasonic probe of claim 1, wherein the heat dissipating member comprises a radiation fin configured to be in contact with the heating element to exchange heat with the heating element.

7. The ultrasonic probe of claim 1, wherein the sealing member comprises an O-ring.

8. The ultrasonic probe of claim 1, wherein when a traveling direction of the echo signal transmitted from and received by the acoustic module is a first direction, the hole and the heating element are disposed along a second direction intersecting the first direction.

9. The ultrasonic probe of claim 1, wherein the housing comprises at least one hollow portion, and the hole is formed on one surface of the hollow portion.

10. The ultrasonic probe of claim 1, wherein the housing comprises a recessed portion recessed toward the inside of the housing, and the hole is formed on one surface of the recessed portion.

* * * * *